United States Patent [19]

Kubo et al.

[11] Patent Number: 4,888,339
[45] Date of Patent: Dec. 19, 1989

[54] AGENT FOR PROPHYLAXIS AND TREATMENT OF CARDIAC HYPERTROPHY

[75] Inventors: Masami Kubo, Osaka; Takashi Ochiai, Kobe; Hirofumi Yuasa, Amagasaki, all of Japan

[73] Assignee: Tanabe Seiyaku Co., Ltd., Osaka, Japan

[21] Appl. No.: 130,464

[22] Filed: Dec. 9, 1987

[30] Foreign Application Priority Data

Dec. 9, 1986 [JP] Japan .................................. 61-294574

[51] Int. Cl.⁴ .................. A61K 31/415; C07D 233/38
[52] U.S. Cl. .................................. 514/392; 514/398; 548/321
[58] Field of Search .................. 514/392, 398; 548/321

[56] References Cited

U.S. PATENT DOCUMENTS 4,416,895 11/1983 Thorogood .......................... 514/398
4,508,727 4/1985 Yoneda et al. ...................... 514/398
4,587,258 5/1986 Gold et al. ........................... 514/414

FOREIGN PATENT DOCUMENTS 0078545 5/1983 European Pat. Off. ............ 514/392
0095163 11/1983 European Pat. Off. .
6013715 1/1985 Japan .
61-158968 7/1986 Japan .

Primary Examiner—Prince E. Willis
Assistant Examiner—Christine A. Skane
Attorney, Agent, or Firm—Birch, Stewart, Kolasch & Birch

[57] ABSTRACT

Novel agent for the propylaxis and treatment of heart failure, which comprises as an active ingredient a 2-oxo-imidazolidine compound of the formula:

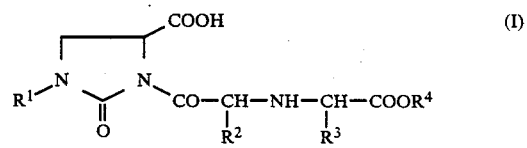

wherein $R^1$ and $R^2$ are the same or different and are each a lower alkyl group, $R^3$ is a phenyl-substituted lower alkyl group, and $R^4$ is a hydrogen atom or a lower alkyl group, or a pharmaceutically acceptable salt thereof.

7 Claims, No Drawings

AGENT FOR PROPHYLAXIS AND TREATMENT OF CARDIAC HYPERTROPHY

This invention relates to a novel agent for the prophylaxis and treatment of heart failure, more particularly, to an agent for the prophylaxis and treatment of heart failure which comprises as an active ingredient a 2-oxo-imidazolidine compound of the formula:

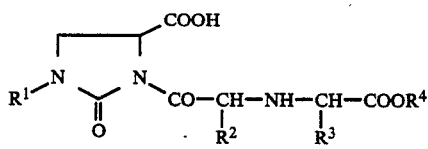

(I)

wherein $R^1$ and $R^2$ are the same or different and are each a lower alkyl group, $R^3$ is a phenyl-substituted lower alkyl group, and $R^4$ is hydrogen atom or a lower alkyl group, or a pharmaceutically acceptable salt thereof.

TECHNICAL BACKGROUND AND PRIOR ART

It is known that heart failure is a clinical syndrome characterised by distinctive symptoms resulting from cardiac output insufficient for needs of body organisms and is mostly induced by cardiac hypertrophy due to excessive load onto myocardium. That is, the cardiac hypertrophy induces change of myocardiac microstructure, failure of energy production mechanism with respect to myocardiac systole and increase of myocardiac oxygen consume, which induce in turn myocardiac hyposystole (cf. "Naikagakusho" (Internal Medical Text), Vol. 2, pages 66-69, issued by Yamanaka Shoten, Feb. 5, 1982). Besides, clinically, due to myocardiac hyposystole, cardiac output is decreased and thereby input into ventricle is disturbed, which induces venous congestion and pulmonary congestion, and then, symptoms such as dyspnea and systemic edema appear.

For the treatment of the heart failure with avoiding myocardiac hyposystole, there have hitherto been used digitalis medicaments having cardiotonic activity such as digitoxin, digoxine, etc., and xanthine medicaments such as caffeine, theophylline, etc. However, the digitalis medicaments have some problems in applicable diseases. That is, although the digitalis medicaments are well effective for low output heart failure, i.e. in the symptoms where the cardiac output is absolutely insufficient for body's needs, they are not so effective for high output heart failure, i.e. in the symptoms where the deficiency of cardiac output is comparatively low. Moreover, contrary to most other medicaments, the digitalis medicaments have less difference between the effective dose and the dose at which they show undesirable side effects, and when the medicaments are continuously administered, there are induced so-called digitalis toxicosis such as nausea, headache, bradycardia, extrasystole, anginal symptom, and the like. Besides, xanthine medicaments have advantageously both of cardiotonic and diuretic activities, but these activities are very weak, and hence, they are not so effective.

OBJECT OF THE INVENTION

The present inventors have intensively studied to obtain a new agent for the prophylaxis and treatment of the heart failure which is effective owing to different activity from the cardiotonic activity of the digitalis and xanthine medicaments, and have found that some imidazolidine compounds are effective for inhibiting or ameliorating cardiac hypertrophy and thereby are useful as an agent for the prophylaxis and treatment of heart failure.

An object of the invention is to provide a novel type of a medicament for the prophylaxis and treatment of heart failure. Another object of the invention is to provide an agent for the prophylaxis and treatment of heart failure according to an inhibitory activity on cardiac hypertrophy. These and other objects and advantages of the invention will be apparent to those skilled in the art from the following description.

DETAILED DESCRIPTION OF THE INVENTION

The agent for the prophylaxis and treatment of heart failure of this invention comprises as an active ingredient a 2-oxo-imidazolidine compound of the formula (I) or a pharmaceutically acceptable salt thereof.

The active compound includes the compounds of formula (I) wherein $R^1$ is an alkyl group having 1 to 4 carbon atoms, such as methyl, ethyl, n-propyl, isopropyl, n-butyl, isobutyl, etc.; $R^2$ is an alkyl group having 1 to 4 carbon atoms, such as methyl, ethyl, n-propyl, isopropyl, n-butyl, isobutyl, etc.; $R^3$ is a phenyl-substituted alkyl group having 1 to 4 carbon atoms in the alkyl moiety, such as benzyl, phenethyl, phenylpropyl, phenylbutyl, etc.; and $R^4$ is hydrogen atom, or an alkyl group having 1 to 4 carbon atoms, such as methyl, ethyl, n-propyl, isopropyl, n-butyl, isobutyl, etc.

Preferred compounds are the compounds of the formula (I) wherein $R^1$ is methyl, $R^2$ is methyl, $R^3$ is phenethyl, and $R^4$ is hydrogen atom or ethyl.

The compounds (I) of this invention contain three asymmetric carbons within the molecule and hence include four diastereoisomers and eight optical isomers. This invention includes these isomers. Among these isomers, however, the compounds particularly suitable for the intended medical use are the compounds of the formula (I) wherein the carbon atoms at the 4-position of the oxoimidazolidine ring and at 2-position of the amino acid moiety of the formula: —NH—CH($R^3$)COOR$^4$ are both S-configuration. Other compounds suitable for the medical use are compounds of the formula (I) wherein the carbon atoms at 4-position of the oxoimidazolidine ring, at 2-position of the alkanoyl moiety of the formula: —COCH($R^2$)— and at 2-position of the amino acid moiety of the formula: —NH—CH($R^3$)COOR$^4$ are all S-configuration.

The 2-oxo-imidazolidine compounds (I) or a pharmaceutically acceptable salt thereof have an activity of inhibiting and ameliorating cardiac hypertrophy and an inhibitory and ameliorating activity on myocardiac hyposystole, and hence, these compounds can be used for the prophylaxis and treatment of heart failure (e.g. congestive heart failure, complementary heart failure, etc.) and also various symptoms accompanied to heart failure, such as congestions of various organs (e.g. lung, liver, etc.), dyspnea, pulmonary edema, systemic edema, peripheral cyanosis, paroxysmal nocturnal dyspnea, cardiac asthma, and the like in a warm-blooded animal including human beings. Moreover, symptoms such as edema, pulmonary circulation disorder, hypertension, valvular disease of the heart, and the like induce cardiac hypertrophy which tends to cause heart failure, and hence, the compounds of this invention are also useful for the prophylaxis of heart failure in the patients having such symptoms as above.

For instance, when (4S)-1-methyl-3-[(2S)-2-[N-((1S)-1-ethoxycarbonyl-3-phenylpropyl)amino]propionyl]-2-oxo-imidazolidine-4-carboxylic acid was orally administered to a model animal suffering from hypertension with characteristic syndrome of enlargement of heart, i.e. spontaneously hypertensive rats, at a dose of 5 mg/kg/day for 10 weeks, the compounds significantly inhibited increase of heart weight, i.e. showed significant activity of inhibiting cardiac hypertrophy. Likewise, when (4S)-1-methyl-3-[(2S)-2-[N-((1S)-1-carboxy-3-phenylpropyl)amino]propionyl]-2-oxo-imidazolidine-4-carboxylic acid was intraperitoneally administered to the rats at a dose of 0.5 mg/kg, similar activity was obtained.

Moreover, the compounds (I) of this invention have low toxicity. For instance, when (4S)-1-methyl-3-[(2S)-2[N-((1S)-1-carboxy-3-phenylpropyl)amino]propionyl]-2-oxo-imidazolidine-4-carboxylic acid or (4S)-1-methyl-3-[(2S)-2[N-((1S)-1-ethoxycarbonyl-3-phenylpropyl)amino]propionyl]-2-oxo-imidazolidine-4-carboxylic acid was orally administered to rats at a dose of 5 g/kg, even after observing for 5 days, no rats was died.

The compounds (I) used as an active ingredient in this invention may be used in any form of a free acid (and/or free base) or a pharmaceutically acceptable salt thereof. The free acid (or base) can be converted into its salt by treating it with an organic or inorganic acid or alternatively with an organic or inorganic base in a usual manner. The pharmaceutically acceptable salts of the compounds (I) include organic acid addition salts (e.g. succinate, maleate, fumarate, methanesulfonate, etc.), inorganic acid addition salts (e.g. hydrochloride, hydrobromide, sulfate, phosphate, etc.), salts with organic bases (e.g. lysine salt, ornithine salt, etc.), and salts with inorganic bases (e.g. sodium salt, potassium salt, calcium salt, magnesium salt, etc.).

The prophylactic and therapeutic agents of the invention containing as an active ingredient a compound (I) or a pharmaceutically acceptable salt thereof can be administered by oral route or by parenteral route. The dose of a compound (I) or a pharmaceutically acceptable salt thereof may vary depending on the severity of diseases, age, weight and body conditions of the patients and the like, but is usually in the range of 0.05 to 100 mg/kg/day, preferably 0.1 to 25 mg/kg/day, in case of oral administration, and in the range of 1 $\mu$g/kg/day to 2 mg/kg/day, preferably 1 $\mu$g/kg/day to 0.5 mg/kg/day, in case of parenteral administration.

The compounds (I) or their pharmaceutically acceptable salts may be used in the form of conventional pharmaceutical preparations in admixture with conventional pharmaceutically acceptable carrier or diluent which are usually used for the pharmaceutical preparations suitable for oral or parenteral administration. The pharmaceutically acceptable carriers or diluents include, for example, starch, lactose, glucose, potassium phosphate, corn starch, gum arabic, magnesium stearate, and the like. The pharmaceutical preparations include solid preparations such as tablets, pills, capsules, suppositories, and the like, and liquid preparations such as solutions, suspensions, emulsions, and the like. These preparations may be sterilized and may optionally contain other additives, such as stabilizers, wetting agents, emulsifiers, and the like.

The compounds (I) can be prepared by the method as disclosed in European Patent Publication No. 95163 (A2).

The pharmacological activities of the compounds of this invention are illustrated by the following experiments.

EXPERIMENT 1

Activity for inhibiting cardiac hypertrophy:

[Method]:

The test compound: (4S)-1-methyl-3-[(2S)-2-[N-((1S)-1-ethoxycarbonyl-3-phenylpropyl)amino]propionyl]-2-oxo-imidazolidine-4-carboxylic acid hydrochloride was dissolved in distilled pure water and orally administered to spontaneously hypertensive rats (SHR) (4 weeks old age at the beginning of experiment, groups of 6 rats) at a dose of 5 mg/kg/day for 10 weeks.

Twenty-four hours after the final dosing, the SHR was killed by bleeding under ether anesthesia. The weight of heart was measured and the weight of heart per 100 g of body weight (relative heart weight) was calculated. After that, the heart was used for the measurement of cross sectional area of the heart.

Method for measurement of cross sectional area of heart is as follows:

(i) After weighing the excised heart, the excised heart was immersed in 10% neutral buffered formalin solution for about one week to fix said heart. The fixed heart was cut at a definitive region crossing the left and right ventricles to obtain a sample (thickness: about 2 mm). The sample was again immersed in a 10% neutral buffered formalin solution overnight, treated with paraffin in a usual manner (Note 1) and then stained with hematoxyin eosine (HE).

(ii) The microscopic image of the stained sample was examined by an image analyzer (Note 2) to give the ratio of the area of stained region to the area of unstained region (the latter area being the gap produced in preparing the sample).

(iii) The real area of the sample was obtained by an image analyzer and then multiplied by the ratio obtained in the above (ii) to give the cross sectional area of the heart.

[Note 1]: It is disclosed in "Byori Gijutsu Mannual" (Mannual for Pathorogical Technology) 3, Technology for Histopathorogical Preparation, ed. by Nippon Byori Gakkai, issued on Mar. 30, 1981 by Ishiyaku Shuppan K.K.

[Note 2]: Nikon three tube color television camera and Nikon Ruzex II, manufactured by Nippon Kogaku K.K.

[Results]:

The results are shown in Table 1.

TABLE 1

|  | Relative heart weight (g) | Sectional area of heart (mm$^2$) |
|---|---|---|
| Non-administ. group | 0.399 ± 0.01 | 66.8 ± 4.0 |
| Test sample-administ. group | 0.34 ± 0.01* | 57.9 ± 2.9* |
| Inhibitory ratio (%) | 13 | 13 |

The mark (*) means that the data were significant with a level of significance of 1%.

The inhibitory ratio was calculated by the following equation:

$$\text{Inhibitory ratio (\%)} = \frac{\begin{bmatrix}\text{Value in non-}\\\text{administ. group}\end{bmatrix} - \begin{bmatrix}\text{Value in sample-}\\\text{administ. group}\end{bmatrix}}{\text{Value in non-administ. group}} \times 100$$

As is clear from the above experimental results, the active compound of this invention showed 13% inhibitory ratio in both of the relative heart weight and sectional area of the heart in comparison with the non-administration group and showed clear inhibition of cardiac hypertrophy.

EXPERIMENT 2

Activity for inhibiting cardiac hypertrophy:

[Method]:

The test compound: (4S)-1-methyl-3-[(2S)-2-[N-((1S)-1-carboxy-3-phenylpropyl)amino]propionyl]-2-oxo-imidazolidine-4-carboxylic acid hydrochloride was dissolved in distilled pure water and intraperitoneally administered to spontaneously hypertensive rats (SHR) (4 weeks old age at the beginning of experiment, groups of 9 rats) at a dose of 0.5 mg/kg/day for 10 weeks.

Twenty-four hours after the final dosing, the SHR was killed by bleeding under ether anesthesia. The weight of heart was measured and the weight of heart per 100 g of body weight (relative heart weight) was calculated.

[Results]:

The results are shown in Table 2.

TABLE 2

|  | Relative heart weight (g) |
|---|---|
| Non-administ. group | 0.36 ± 0.013 |
| Test sample-administ. group | 0.33 ± 0.012** |
| Inhibitory ratio (%) | 8 |

The mark (**) means that the data were significant with a level of significance of 0.1%.

As is clear from the above experimental results, the active compound of this invention showed 8% inhibitory ratio of relative heart weight in comparison with the non-administration group and showed clear inhibition of cardiac hypertrophy.

The preparations of the present agent are illustrated by the following Examples.

EXAMPLE 1

Tables:

[Formulation]:

| | |
|---|---|
| (Active ingredient) (4S)-1-methyl-3-[(2S)-2-[N-((1S)-1-ethoxycarbonyl-3-phenylpropyl)amino]propionyl]-2-oxo-imidazolidine-4-carboxylic acid | 10 mg |
| Lactose | 86.8 mg |
| Polyvinylpyrrolidone | 5 mg |
| Corn starch | 37 mg |
| Magnesium stearate | 1.2 mg |
| Totally | 140.0 mg |

[Method]:

To the active ingredient are added lactose and corn starch, and the mixture is well mixed, and thereto is added a solution of polyvinylpyrrolidone in purified water, and the mixture is well kneaded to granulate. The granules thus prepared are dried, and thereto is added magnesium stearate, and the mixture is tabletted in a usual manner to give tablets.

EXAMPLE 2

Tablets:

[Formulation]:

| | |
|---|---|
| (Active ingredient) (4S)-1-methyl-3-[(2S)-2-[N-((1S)-1-carboxy-3-phenylpropyl)amino]propionyl]-2-oxo-imidazolidine-4-carboxylic acid | 10 mg |
| Lactose | 80 mg |
| Polyvinylpyrrolidone | 3.3 mg |
| Corn starch | 35.9 mg |
| Magnesium stearate | 0.8 mg |
| Totally | 130.0 mg |

[Method]:

In the same manner as described in Example 1, the tablets are prepared.

EXAMPLE 3

Injections:

[Formulation]:

| | |
|---|---|
| (Active ingredient) (4S)-1-methyl-3-[(2S)-2-[N-((1S)-1-ethoxycarbonyl-3-phenylpropyl)amino]propionyl]-2-oxo-imidazolidine-4-carboxylic acid | 10 mg |
| Sodium chloride | 9 mg |
| Distilled water for injection | q. s. |
| Totally | 1 ml |

[Method]:

The active ingredient and sodium chloride are dissolved in distilled water for injection, and the solution is filtered with a filter (pore size: 0.22 μm), and filled in ampoules and then sterilized to give injections.

EXAMPLE 4

Injections:

[Formulation]:

| | |
|---|---|
| (Active ingredient) (4S)-1-methyl-3-[(2S)-2-[N-((1S)-1-carboxy-3-phenylpropyl)amino]propionyl]-2-oxo-imidazolidine-4-carboxylic acid | 8.54 mg |
| Sodium chloride | 9.0 mg |
| Sodium hydrogen carbonate | 8.4 mg |
| Distilled water for injection | q. s. |
| Totally | 1 ml |

[Method]:

[Method]:

Sodium chloride is dissolved in distilled water for injection, and thereto is added the active ingredient, and the mixture is dissolved with sodium hydrogen carbonate. The solution is silterd with a filter (pore size: 0.22 μm). The solution is filled in ampoules and then sterilized to give injections.

What is claimed is:

1. A method for the prophylaxis and treatment of cardiac hypertrophy in a warm-blooded animal, which comprises administering to said warm-blooded animal a prophylactically or therapeutically effective amount of 2-oxo-imidazolidine compound of the formula:

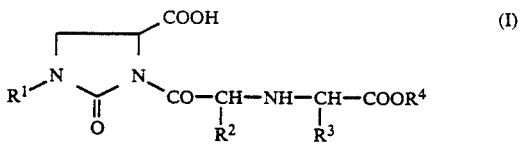

wherein $R^1$ and $R^2$ are the same or different and are each a lower alkyl group, $R^3$ is a phenyl-substituted lower alkyl group, and $R^4$ is hydrogen atom or a lower alkyl group, or a pharmaceutically acceptable salt thereof.

2. The method according to claim 1, wherein the compound to be administered is a compound of formula (I) wherein $R^1$ is an alkyl group having 1 to 4 carbon atoms, $R^2$ is an alkyl group having 1 to 4 carbon atoms, $R^3$ is a phenyl-substituted alkyl group having 1 to 4 carbon atoms in the alkyl moiety, and $R^4$ is hydrogen atom, or an alkyl group having 1 to 4 carbon atoms or a pharmaceutically acceptable salt thereof.

3. The method according to claim 1, wherein the compound to be administered is a compound of the formula (I) wherein $R^1$ is methyl, $R^2$ is methyl, $R^3$ is phenethyl, and R4 is hydrogen atom or ethyl or a pharmaceutically acceptable salt thereof.

4. The method according to claim 1, wherein the compound to be administered is a compound of the formula (I) wherein the carbon atoms at 4-position of the oxoimidazolidine ring and at 2-position of the amino acid moiety of the formula: $-NH-CH(R^3)COOR^4$ are both S-configuration or a pharmaceutically acceptable salt thereof.

5. The method according to claim 1, wherein the compound to be administered is a compound of the formula (I) wherein the carbon atoms at 4-position of the oxoimidazolidine ring, at 2-position of the alkanoyl moiety of the formula: $-COCH(R^2)-$ and at 2-position of the amino acid moiety of the formula: $-NH-CH(R^3)COOR^4$ are all S-configuration or a pharmaceutically acceptable salt thereof.

6. The method according to claim 1, wherein the compound to be administered is (4S)-1-methyl-3-[(2S)-2-[N-((1S)-1-ethoxycarbonyl-3-phenylpropyl)amino]-propionyl]-2-oxo-imidazolidine-4-carboxylic acid or a pharmaceutically acceptable salt thereof.

7. The method according to claim 1, wherein the compound to be administered is (4S)-1-methyl-3-[(2S)-2-[N-((1S)-1-carboxy-3-phenylpropyl)amino]propionyl]-2-oxo-imidazolidine-4-carboxylic acid or a pharmaceutically acceptable salt thereof.

* * * * *